(12) United States Patent
Schwieters et al.

(10) Patent No.: US 10,338,044 B2
(45) Date of Patent: Jul. 2, 2019

(54) METHOD AND APPARATUS FOR REDUCING GAS CONSUMPTION IN CONTINUOUS FLOW ANALYTICAL INSTRUMENTS

(71) Applicant: Thermo Fisher Scientific (Bremen) GmbH, Bremen (DE)

(72) Inventors: Johannes Schwieters, Ganderkesee (DE); Michael Krummen, Bad Zwischenahn (DE); Hans-Juergen Schlueter, Bremen (DE); Oliver Kracht, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 272 days.

(21) Appl. No.: 15/142,909

(22) Filed: Apr. 29, 2016

(65) Prior Publication Data

US 2016/0320362 A1    Nov. 3, 2016

(30) Foreign Application Priority Data

Apr. 30, 2015  (GB) .................................. 1507443.8
May 5, 2015    (GB) .................................. 1507656.5

(51) Int. Cl.
*G01N 30/28* (2006.01)
*B01D 53/02* (2006.01)
(Continued)

(52) U.S. Cl.
CPC ......... *G01N 33/0013* (2013.01); *G01N 30/06* (2013.01); *G01N 33/0021* (2013.01); *G01N 2030/067* (2013.01)

(58) Field of Classification Search
None
See application file for complete search history.

(56) References Cited

U.S. PATENT DOCUMENTS

| 3,357,157 A | 12/1967 | O'Donnell |
| 3,422,665 A | 1/1969 | Haase |
| (Continued) | | |

FOREIGN PATENT DOCUMENTS

| CA | 2455934 A1 | 2/2003 |
| CN | 102770759 A | 11/2012 |
| (Continued) | | |

*Primary Examiner* — Christopher Adam Hixson
*Assistant Examiner* — Michelle Adams
(74) *Attorney, Agent, or Firm* — David A. Schell (57) ABSTRACT

A gas transport system includes at least one chemical reactor having at least one inlet and at least one gas outlet and at least one sample introduction unit for delivering the sample into the chemical reactor. The gas transport system at least one carrier gas line fluidly coupled to the chemical reactor inlet for introducing into the chemical reactor carrier gas from a carrier gas source, at least one gas outlet line from the chemical reactor gas outlet, and at least one gas recycling line connected to the gas outlet and/or the gas outlet line by a first gas line junction that is arranged between the chemical reactor and a downstream detection unit on the gas outlet line. The gas transport system is adapted to allow recycling of at least a portion of gas emerging from the chemical reactor outlet back to the chemical reactor via the gas recycling line.

28 Claims, 3 Drawing Sheets

(51) Int. Cl.
*G01N 33/00* (2006.01)
*G01N 30/06* (2006.01)

(56) References Cited

U.S. PATENT DOCUMENTS

| | | | |
|---|---|---|---|
| 4,230,464 A | 10/1980 | Bonmati et al. | |
| 4,305,906 A * | 12/1981 | Mikasa | G01N 30/40 422/62 |
| 5,522,915 A * | 6/1996 | Ono | G01N 33/0011 266/80 |
| 6,063,166 A | 5/2000 | Wilson | |
| 6,293,995 B2 | 9/2001 | Wilson | |
| 6,627,155 B1 * | 9/2003 | Uemura | G01N 31/12 250/288 |
| 7,928,369 B2 | 4/2011 | Hatscher et al. | |
| 8,308,854 B2 | 11/2012 | McCauley et al. | |
| 2007/0125233 A1 | 6/2007 | Bostrom et al. | |

FOREIGN PATENT DOCUMENTS

| | | |
|---|---|---|
| DE | 4344441 C1 | 7/1995 |
| GB | 2010116 A | 6/1979 |
| WO | 95/18372 A1 | 7/1995 |
| WO | 9836815 A1 | 8/1998 |
| WO | 03/025270 A1 | 3/2003 |
| WO | 2007/112876 A2 | 10/2007 |

\* cited by examiner

METHOD AND APPARATUS FOR REDUCING GAS CONSUMPTION IN CONTINUOUS FLOW ANALYTICAL INSTRUMENTS

FIELD

The invention relates to a continuous gas stream system for analytical instruments, such as but not limited to elemental analyzers. The invention furthermore relates to a method for reducing gas consumption in continuous flow analytical instruments.

BACKGROUND

Elemental analysis is a method for the determination of carbon, nitrogen, hydrogen, oxygen and/or sulphur composition of different materials, including liquids, solids and gases. During elemental analysis, samples are typically converted to simple gases such as $H_2$, $CO$, $CO_2$, $N_2$, $SO_2$, and $H_2O$, usually by combustion or reduction/pyrolysis in a high temperature reactor (usually at about or exceeding 1000° C.), and usually with aid of catalysts to facilitate the combustion. Also a combination of two or more reactors are not uncommon, e.g. one oxidation reactor combined with a reduction reactor to reduce e.g. nitric oxides to nitrogen. The combustion products are carried by an inert carrier gas (e.g. He or Ar) to a detector. The samples can subsequently be transported for further detection or simply vented. To allow quantitative or qualitative determination of each gas species, the mixture is separated, for example in one or more chromatographic columns, such as a gas chromatographic column, or by adsorption/thermodesorption techniques, and detected using for example flame photometric detection, atomic absorption spectroscopy, inductively coupled plasma optical emission spectrometry (ICP-OES), optical absorption spectrometers (e.g. for infrared absorption), mass spectrometers, including inductively coupled plasma mass spectrometry (ICP-MS), glow discharge mass spectrometry (GD-MS), or by mass spectrometers for isotope ratio analysis.

Typical systems comprise a reactor to convert sample material to simple gases, one or more chemical traps to adsorb undesired gas analytes such as $H_2O$, one or more separation columns and a detector. For high reproducibility, the system is permanently flushed with the carrier gas. This is done to maintain pressure and temperature regimes, to avoid introduction of contaminant gases such as air, and to avoid damage to any materials and chemicals within the system and to continuously flush away contamination. Elemental analyzers can require a flow up to, or in excess of, 1000 mL/min, which varies depending on the volume that needs to be flushed. The biggest volume in the system is the combustion and/or reduction or pyrolysis reactor.

In some commonly used systems, a flow rate of 40 to 300 mL/min, or more commonly 80 to 200 mL/min is required. Typical analysis time of a sample is up to 15 minutes. Of this time, the analyte gases pass through the reactor in less than 3 minutes, and for the remaining time, the system is flushed with carrier gas which is usually vented and thus wasted to atmosphere.

The most common carrier gas is helium, but in recent times this gas has become expensive, in part due to less availability. To reduce cost, it is common to reduce helium consumption in elemental analyzers by argon, for example in systems provided by Thermo Fisher Scientific S.p.A (Rodano, Italy), Elementar Analysensysteme (Hanau, Germany), Perkin Elmer (Waltham, Mass., USA) and LECO Corporation (St. Joseph, Mich., USA). However, argon suffers from the disadvantage that it has a high thermal conductivity and high ionization efficiency, which make it particularly unfavourable when a mass spectrometer is used for detection. Additionally, use of argon as carrier gas requires recalibration of volume flow controller and replacing detectors, since current detectors and applications of the systems are adapted to use of helium as carrier gas.

Further helium consumption is needed for purposes of a reference signal in the thermal conductivity detector (TCD) of a typical elemental analyzer. This reference flow of pure helium compares the thermal conductivity of the reference with the mixture of helium and analyte gas that arrives at the detector. The reference flow is also used to purge the sample in the sample injection system (for example autosamplers) before it is injected into the reactor, to remove ambient air. This reference/purge flow of carrier gas thus prevents contaminating gases such as nitrogen oxygen, and water from entering the reactor during injection. The helium purge flow can be as high as 250 mL/min, and is therefore a major source of helium consumption.

WO 98/36815 discloses a carrier gas recycling system for an analytical instruments such as a gas chromatograph, that collects, purifies, compresses and recycles carrier gas. The system includes means to collect a carrier gas along with contaminants, a purifier to remove contaminants from the carrier gas, a compressor to compress the collected and purified gas, a source of a make-up carrier gas, and means to receive recycled, purified gas and introduce the recycled carrier gas into the analytical instrument.

U.S. Pat. No. 6,293,995 discloses a gas chromatograph that includes a closed-loop system for storage and reuse of hydrogen carrier gas. The chromatograph includes a gas storage system that receives a gas output from a detector, and stores the gas for subsequent reuse. The storage system preferably includes a metal hydride storage system.

In U.S. Pat. No. 8,308,854, a system for recycling helium gas is disclosed, that includes a bladder to receive helium-bearing gas from a vent of a gas chromatograph, a source of pressurized air or gas to supply gas into a compartment containing the bladder so as to compress the bladder containing the helium bearing gas, a gas reservoir coupled to the bladder interior so as to receive the helium bearing gas, and at least one purification module for removing contaminants from the helium bearing gas, and an output for coupling the purification module to a carrier gas inlet of the gas chromatograph.

The present invention has been made against this background, to provide an improved and flexible system that consumes less carrier gas than systems previously described in the art. The invention further provides a method of elemental analysis that requires reduced gas consumption.

SUMMARY

The invention provides a gas stream system with reduced carrier gas consumption, that does not require changing the type of carrier gas that is used in existing detectors and applications that are adapted for use with specific gas (usually helium). The invention is based on the idea that by splitting the flow of gas downstream from a sample receptacle or chamber (e.g. reactor) and redirecting the majority of the gas flow from the receptacle back towards the inlet of the receptacle and/or towards the sample injection system, a large proportion of carrier gas may be recycled, leading to overall reduced carrier gas consumption.

In elemental analysis systems, high gas flows are commonly only required during sample conversion in large volume reactors. Subsequent components of the analytical system, including separation columns and detectors are generally adapted for low flow rates and can therefore be flushed with lower gas flow rates than the reactor. For this purpose, the inner diameter of the separation column may be reduced. Since constant system conditions are favorable for optimal analytical conditions, and thus the reproducibility of analyses, a sufficient gas flow must be ensured in the reactor/sample chamber, while maintaining the rest of the system at constant and usually low flow rates. When flushing the reactor with a high gas volume, this means that a large proportion of the gas used during the flushing period must be vented to atmosphere.

The system according to the invention provides for carrier gas recycling, and thus lower gas consumption, while ensuring that analyte gases, i.e. sample gases or analyte gas generated from the sample in a reactor is (i) transferred to the detector without sample loss or any change of analytical information provided by the sample, and (ii) not redirected into the reactor/sample chamber, where it could contaminate following samples being analyzed. Further, the system can in useful embodiments provide for a standby mode during idle times of the instrument, during which constant gas flow is maintained while gas consumption is minimized, so as to prevent damage to hardware during standby, and allow for return to operating conditions in the system in a short time.

Thus, in a first aspect the invention provides a gas transport system for a continuously flushed analytical apparatus, comprising
 (i) at least one receptacle for analyte gas having at least one inlet for introducing at least one sample and at least one carrier gas into the receptacle, and at least one gas outlet, for releasing analyte gas and carrier gas from the receptacle;
 (ii) at least one sample introduction unit, for delivering the sample into the receptacle;
 (iii) at least one carrier gas line fluidly coupled to the receptacle inlet for introducing into the receptacle carrier gas from a carrier gas source;
 (iv) at least one gas outlet line from the receptacle gas outlet; and
 (v) at least one gas recycling line connected to the gas outlet and/or the gas outlet line by a first gas line junction, and connected to the sample introduction unit and/or the inlet and/or the carrier gas inlet line at a second gas line junction.

The gas transport system can therefore be adapted to allow recycling of at least a portion of gas emerging from the receptacle outlet back to the receptacle or sample introduction unit via the gas recycling line.

The invention can also be extended to provide such a gas transport system in, or in combination with, an elemental analyzer. In such embodiments, the receptacle may be a reactor for combustion, reduction or pyrolysis of the sample.

According to a further aspect of the invention, there is provided an elemental analyzer having a system for recycling gas as described herein.

A further aspect of the invention provides a method for managing gas consumption in a continuously flushed apparatus, the method comprising steps of:
 (i) streaming carrier gas through at least one carrier gas inlet line into at least one receptacle,
 (ii) introducing at least one sample from at least one sample introduction unit into the receptacle,
 (iii) directing gas from at least one gas outlet on the receptacle through at least one gas outlet line,
 (iv) splitting the flow of gas at a first gas flow junction in the gas outlet line to direct a portion of the gas stream to at least one gas recycling line leading to the carrier gas inlet line and/or the sample introduction unit and/or the receptacle, and a remaining portion of gas onwards through the gas outlet line.

A separation device, in the present context, is a device for separating components of samples. Usually a separation device is a device that separates molecular components of a sample, i.e. the device separates one or more molecular species from other one or more molecular species within a sample of such species. In some embodiments, the separation device is a gas chromatographic column.

An analyte gas, in the present context, is a gas that contains at least one component that is to be analyzed. An analyte gas can for example be a sample gas. In certain embodiments however, e.g. when the sample is not in gaseous form and/or not in the molecular form suitable for the detector used, the sample needs to be reacted to suitable analyte gas.

A gas line, in the present context, refers to any channel, tube, conduit, capillary or the like for transporting gas. It will be apparent to the skilled person that additional components can be arranged on the gas line, such as junctions, valves, flow restrictions, flow controllers, gauges and the like. These components can sometimes also be in fluid connection with the gas line. Gas lines that are herein described as being connected can be directly connected, or they can be fluidly connected through suitable means that are known to the skilled person.

In the present context, a splitter is a construction on a gas line that serves the purpose of splitting a flow of gas. A splitter can comprise a split line, that is a gas line for diverting gas away from another gas line. The two gas lines, the split line and the gas line, meet at a junction where the two lines are in fluid communication. The split ratio is determined by the restrictions following downstream the two lines.

In one embodiment, the gas recycling line, e.g. at one of its ends, can be connected to the gas outlet by a first gas line junction. In another embodiment the gas recycling line can be connected to the gas outlet line by a first gas line junction. In some embodiments, the gas recycling line, e.g. at its other end, is connected to the sample introduction unit at a second gas line junction. In some embodiments, the gas recycling line is connected to the inlet at a second gas line junction. In some embodiments, the recycling line is connected to the gas inlet line at a second gas line junction. In one preferred embodiment, the gas recycling line is connected to the gas outlet line or gas outlet at a first gas line junction, and to the carrier gas line at a second gas line junction. The recycling line can also be simultaneously connected to the sample introduction unit, the inlet and/or the gas inlet line through multiple gas line junctions, e.g. multiple second gas line junctions.

The analyte gas is preferably provided in a carrier gas. The carrier gas can be a suitable inert gas, such as helium or argon. In some embodiments, the carrier gas is provided by a carrier gas line that comprises a gas reservoir that is arranged in fluid communication with the carrier gas line. The gas reservoir is therefore provided in-line with the carrier gas line. The recycling line can be connected to the gas reservoir at a second gas line junction, such that gas recycling occurs into the gas reservoir.

The analyte gas can be provided by a chemical reactor, for example a chemical reactor or chemical furnace of an elemental analyzer.

A receptacle, in the present context, is a volume that is suitable for receiving, generating and/or delivering an analyte gas. In some preferred embodiments, the receptacle is a reactor in which a sample is reacted to form an analyte gas. The reactor can for example be an elemental analysis reactor, such as a combustion reactor, a reduction reactor or a pyrolysis chamber. The reactor preferably comprises a heatable reactor or furnace. In some embodiments, the analyte gas may be delivered to the receptacle as a sample gas, i.e. without requiring conversion in a reactor.

The gas recycling line can be connected to the gas outlet line or the gas outlet at a first gas line junction, and to the carrier gas inlet line at a second gas line junction. In some preferred embodiments, the gas recycling line is connected to the gas outlet line. The second gas line junction can in some embodiments be arranged at, or in fluid communication with, the carrier gas inlet line. In some other embodiments, the second gas line junction is arranged at, or in fluid communication with, the sample introduction unit. The second gas line junction can also be located at, or be in fluid communication with, the receptacle, for example through a gas inlet on the receptacle.

Analyte gas in the system or method according to the invention can be any gas that is supplied or generated in an analytical system. The supply of analyte gas can therefore be any suitable analytical system that provides analytes for separation and/or detection. In some embodiments, the receptacle is an elemental analysis reactor, and the analyte gas is a gas that is generated in the elemental analysis reactor. Such gases include for example $N_2$, $CO_2$, $SO_2$, $CO$ and $H_2$. Analyte gas can also include $H_2O$, which in some configurations is not desirable and can therefore in useful embodiments be removed by means of a chemical trap.

The at least one inlet on the receptacle can be provided as a single inlet, to which an inlet line for delivering sample in a stream of carrier gas is connected. The at least one inlet can also be provided as two or more inlets, wherein sample is delivered through one or more inlets and carrier gas is delivered through one or more inlets. The sample can in general be provided as any solid, liquid or gaseous sample, or as a mixture of solid, liquid and/or gaseous samples. Liquid samples can be provided as a stream or a spray, e.g. comprising droplets of the liquid. In some embodiments, the sample can be converted into a gas sample in the receptacle, resulting in the formation of analyte gas. When the system is used with an elemental analysis reactor, the sample or mixture of samples is reacted to produce gaseous analyte gas such as $N_2$, $CO_2$, $CO$, $H_2$ or $SO_2$, that is delivered through the outlet of the reactor.

The sample introduction unit can be any device for introducing samples into the receptacle for further reaction and/or analysis. The sample introduction unit can in some embodiments comprise a sample introduction device, for delivering/introducing a sample into the receptacle, and a gas purge line, for purging samples and void volume in the sample introduction device with a stream of gas. The sample introduction device can preferably be provided as an autosampler, that can provide automatic delivery of solid, liquid or gaseous samples into the receptacle. The sample introduction device can preferably be purged with an inert gas. The gas is preferably also a gas that is not analyzed in the system, so as to avoid contamination of samples in the sample introduction device that remain to be analyzed, by the gas purge. Preferably, the purge gas in the purge gas line is the same as the carrier gas of the system, such as helium or argon.

Gas in the gas purge line can in certain embodiments be provided by a gas reservoir that is arranged in fluid communication with the gas purge gas line. The same gas reservoir can be used for delivering gas into the carrier gas line and the gas purge line. Alternatively, separate gas reservoirs can be arranged, for delivering gas into the carrier gas line and the gas purge lines, respectively.

Carrier gas and/or purge gas can be provided by a carrier gas supply and/or a purge gas supply, respectively. Accordingly, the system can further comprise at least one gas supply for providing gas into the carrier gas line and/or the gas purge line. In some embodiments, the carrier gas is helium or argon. The carrier gas supply can be provided by a suitable storage medium, such as a helium tank or an argon tank.

The system can comprise one more flow control means on the carrier gas line, to regulate flow of gas to and in the carrier gas line and/or the gas purge line. In some embodiments, flow control means is provided on the carrier gas line and on the gas purge line. In some embodiments, the same flow control means can control gas flow in the carrier gas line and the gas purge line. There can also be arranged a flow controller on the gas recycling line, for regulating gas flow in the gas recycling line.

Flow control means can in general be provided by any flow controller or regulated valve. Flow control means can for example be a mass flow controller or proportional valve, a volume flow controller, or a switchable combination of fixed flow restrictions that allow flow to be adjusted in discrete steps. Such flow control means are described in e.g. U.S. Pat. No. 7,928,369 and WO 2007/112876. Flow control means can be manually or automatically operated. They can also comprise one or more automatic or manual pressure regulator that is combined with at least one flow restriction downstream of the pressure regulator. Flow control means can be an automatic, electronic or digital flow controller, for example as disclosed in WO 2007/112876. An example of flow control means is the ConFloIV™ from Thermo Scientific.

The recycling line can be connected to the gas purge line at a second gas line junction. Through such a connection, gas that is delivered into the recycling line can be used as purging gas, for purging the sample introduction device. This arrangement results in less purge gas consumption in the system, because a portion of the gas that is delivered through the outlet of the receptacle is recycled back into the gas purge line.

One or more valves can be arranged in the system, for controlling flow of gas in the carrier gas line, the purge line, the gas outlet line and/or the recycling line. For example, there can be one or more valves arranged on, or in fluid communication with, the recycling line. In some embodiments, the one or more valves is arranged at a gas line junction, such as the first line junction and/or the second line junction. In one embodiment there is a valve arranged on the gas recycling line, for controlling gas flow in the gas recycling line. The valve can also be arranged in fluid communication with the gas recycling line. In one embodiment, the valve is a switch valve that has one position in which gas is able to flow through the gas recycling line and another position in which gas is prevented from flowing through the gas recycling line.

It can be preferable to arrange a purification unit on the gas recycling line, for removing unwanted species. Such purification unit can suitably be a trap, and can in some embodiments be, but is not limited to, a chemical trap, a dryer (e.g. such as from Nafion®), a cold trap, or adsorption trap. In some embodiments, the purification unit removes residual water and/or $CO_2$ that otherwise might contaminate samples in the sample introduction device. Accordingly, in some embodiments, there is at least one purification unit, such as but not limited to a chemical trap, arranged on the gas recycling line. The purification unit is preferably arranged downstream from a valve for controlling gas flow in the recycling line, between the valve and the second gas line junction.

There can be arranged an open vent on the recycling line, for venting gas in the recycling line to atmosphere. The vent is preferably fluidly connected to the recycling line. There can be a valve arranged at the open vent, or in fluid communication with the vent, for controlling gas flow through the vent. In one embodiment, the valve is a switch valve that is located on, or in fluid communication with the gas recycling line and the gas vent, the valve having a first position, in which gas is prevented from flowing through the vent and gas is allowed to flow through the gas recycling line, and a second position in which gas is allowed to flow through the gas vent and gas is prevented from flowing through the gas recycling line towards the sample delivery unit and/or the carrier gas line. Thereby, gas that enters the gas recycling line can be vented to air rather than reused in the receptacle and/or the sample introduction unit (e.g., autosampler). This can be useful, especially during and/or following sample delivery to the receptacle, so as avoid contamination of following samples. Venting to atmosphere can also be useful for avoiding sample overloading on the separation column.

The switch valve thus arranged can therefore serve the dual purpose of controlling gas flow through the open vent and gas flow through the recycling line.

There can also be arranged a compressor or pump on the recycling line. This is especially useful in an arrangement in which the recycling line feed into a gas reservoir that is maintained at slight overpressure, e.g. 2-3 bars. Such a reservoir can for example be arranged in fluid communication with the carrier gas line, and can provide a source of gas for the carrier gas line and/or the gas purge line. Since gas that enters the gas recycling line is typically at or near atmospheric pressure, it will be necessary to arrange a compressor on, or in fluid communication with, the recycling line, to maintain the gas reservoir at overpressure during recycling. A controller can be arranged on the recycling line, that receives input from a pressure gauge on the gas reservoir, and provides a signal to the compressor to maintain a desired pressure in the gas reservoir. In such a configuration, it may also be desirable to arrange a flow controller on the recycling line, e.g. a mass or volume flow controller.

In some embodiments, there can be a need for flushing of the sample introduction device (e.g., an autosampler) prior to introduction of sample into the receptacle, e.g. an elemental analysis chamber or elemental analysis furnace, to ensure that delivery of sample does not introduce contaminating gases. The flushing can be augmented by recycling a portion of the carrier gas that is flushed through the receptacle through the recycling line and into the sample introduction device. Preferably, a large portion of the carrier gas that is streamed through the receptacle is recycled in this fashion prior to sample introduction. Following the introduction of sample into the receptacle, gas flow through the recycling line can be reduced or completely prevented. This is done to reduce the overall consumption of carrier gas. The sample in the sample introduction unit is then flushed with a reduced amount of gas until shortly before it is injected for the subsequent analysis. This "reduced carrier gas flow" mode can be maintained until there is little or no sample left in the flow of carrier gas from the receptacle, at least in the flow upstream of the junction on the outlet or outlet line with the recycling line. When a sufficiently low concentration of sample gas has been reached in the carrier gas, the recycling line can be opened to recycling. Polar gases such as e.g. CO2 and SO2 need more time to flush out of the system, but in embodiments where a trap (chemical trap or other trap) is arranged in the recycling line, recycling can be allowed even if there is some background concentration of such gases still in the stream from the receptacle, if the concentration of such gases is sufficiently low downstream of such trap. As described as an option in the above, the prevention of gas flow through the recycling line can be done by venting gas that enters the recycling line to atmosphere by means of a switch valve that controls gas flow into an open vent on the recycling line. Thus, by venting, not recycling, the directed gas flow from the gas bypass line until substantially all sample has disappeared from the gas flow, contamination of following samples can be prevented. "Substantially all" as used herein is to be understood in the context of the respective apparatus and analysis employed, when "substantially all" sample has disappeared this means that any remaining sample is less than would interfere with subsequent analysis.

During and/or following sample introduction, and typically until all sample or analyte gas has been detected, it is also possible to prevent gas flow through the recycling line and simultaneously reduce flow of carrier gas through the system, e.g. by reducing the carrier gas flow rate into the receptacle using a flow controller. This will direct all gas that flows from the receptacle towards the detection unit, and thus directing the flow of gas through the at least one separation unit and to the at least one detector. In this way, preferably the gas flow through the analytical portion of the system such as the separation device and/or detector remains constant and contamination of the receptacle via the recycling line is prevented.

Flow rates in gas lines of the system, such as the gas purge lines, the gas recycling line and/or the gas outlet line can in general be in the range of 10 to 1000 mL/min. In some preferred embodiments, the flow rate in the gas purge line during purging can be in the range of 20 to 800 mL/min, in the range of 30 to 600 mL/min, in the range of 40 to 400 mL/min, in the range of 100 to 300 mL/min, in the range of 150 to 250 mL/min, or about 200 mL/min. Flow rates in the carrier gas line can be in the range of 5 to 500 mL/min, such as 5 to 400 mL/min, 5 to 300 mL/min, 5 to 200 mL/min, or 5 to 100 mL/min. Flow rates in the gas outlet line, downstream from the first gas line junction, can be in the range of 5 to 500 mL/min, such as 5 to 400 mL/min, 5 to 300 mL/min, 5 to 200 mL/min, 5 to 100 mL/min, 5 to 50 mL/min or 5 to 30 mL/min.

Accordingly, in some embodiments, the gas recycling line is configured so that when total gas flow from the receptacle outlet is in the range of about 80 to about 1000 mL/min and preferably in the range of about 100 to about 300 mL/min, a gas flow that is in the range of about 5-35 mL/min and preferably in the range of 10-20 mL/min pass through said first gas line junction onwards through the gas outlet line during recycling.

As should be appreciated, the system can be configured so as to split away a desired portion of gas in the gas outlet line into the gas recycling line. By selecting gas lines of appropriate dimensions and/or by arranging flow controllers to control flow in the gas outlet line and/or the recycling line, any desired portion of the gas flow can be recycled through the gas recycling line.

In general, the gas transport system according to the invention is part of a continuous flow system, i.e. there is always gas flow through the receptacle towards a detection unit, that can comprise at least one separation unit, e.g. a separation column or the like, for separating analyte gas species (e.g., different analyte gases such as $N_2$, $CO_2$, CO, $H_2$ and/or $SO_2$), and at least one detector. Therefore, during splitting of gas stream in the gas outlet line into the gas recycling line, gas that is directed onwards through the gas outlet line will flow into a detection unit. Accordingly, in some embodiments, the gas recycling line is configured so that during recycling, in the range of about 1-50 vol % of gas from the receptacle gas outlet is directed onwards through the gas outlet line and in the range of 50-99 vol % of gas from the receptacle outlet is directed to the gas recycling line, and preferably in the range of about 2-40 vol %, such as in the range of about 2-33 vol % and more preferably in the range of about 5-25 vol % of gas from the receptacle gas outlet is directed onwards through the gas outlet line, such as in the range 5-20 vol %, or in the range 10-20 vol %, such as about 15 vol % or about 20 vol %, and in the range of 95-75 vol % of gas from the receptacle outlet is directed to the gas recycling line. Preferably at least 50%, or at least 60%, or at least 70%, or at least 80%, or at least 90% of the gas flow from the receptacle can be redirected into the gas recycling line.

The detection unit is preferably connected to the gas outlet line downstream of said first gas line junction, such that there is at least one separation unit, e.g. gas chromatography column, arranged downstream of the first gas line junction and at least one detector downstream of said separation unit. In some embodiments, there are two separation units, for example two gas chromatography columns arranged in series. A trap, such as but not limited to a chemical trap, drying trap (dryer), cold trap, or adsorption trap, can also be arranged upstream from the at least one separation unit, downstream from the first gas line junction.

The detector can be any detector that is useful for analytical application of gas samples. For example, the detector can be selected from the group consisting of a mass spectrometer, a thermal conductivity detector, and an optical spectrometer. In some preferred embodiments, the detector is a thermal conductivity detector. In some embodiments, the detector is a mass spectrometer. In some embodiments, there are two detectors arranged, for example a thermal conductivity detector followed by a mass spectrometer.

In another embodiment of the invention there is provided a bypass gas line that can be arranged on the gas outlet line, downstream from the separation unit. The bypass gas line can be provided by splitting away a part of the gas stream from the separation unit, through a gas splitter, e.g. a bypass gas line that is connected to the gas outlet line downstream from the separation device. Accordingly, there can be a gas flow splitter provided downstream of the separation unit, splitting a gas flow stream exiting the separation unit into a gas stream entering a bypass line and a gas stream entering the detector. The bypass gas line can be fluidly connected to the gas recycling line. There can be a valve arranged on the bypass gas line, for controlling gas flow in the bypass gas line. The valve can be a switch valve, connecting the bypass line to the gas recycling line, the switch valve having at least two positions wherein a first position allows flow from the first gas flow junction through the recycling line and prevents flow of gas from the bypass line to the recycling line, and a second position preventing flow from the first gas line junction to the recycling line and allowing flow from the bypass line to the recycling line. Accordingly, the valve can regulate gas flow through the recycling line, towards the carrier gas line, the sample introduction unit (e.g., autosampler), or gas purge line, as well as regulate gas flow through the bypass line. The valve is preferably provided upstream from any flow controllers, traps or compressors that can be arranged on the gas recycling line.

The bypass gas line can be useful for venting a part of the gas stream downstream from the separation unit to atmosphere. This can be done through an open vent that can be arranged on the bypass line or recycling line, and that can be regulated by a valve on, or in fluid communication with, the vent and/or the gas recycling line. This feature can be useful for concentrating analyte gases on the separation column, while maintaining a constant gas flow into the detector. Thus, a portion of gas flow through the separation column can be split away through an open bypass gas line and vented to air through an open vent on the gas recycling line or bypass line. During this time, gas flow into the recycling line through the first gas line junction is prevented by the split valve that regulates flow in the gas recycling line and the bypass gas line. After a sample has been loaded onto the separation unit, e.g. a separation column, gas flow through the bypass gas line can be prevented and simultaneously gas flow through the gas recycling line can be allowed by changing position of the switch valve. This leads to a decreased gas flow through the separation unit, which means that analyte gases on the separation unit will emerge from the unit at an increased concentration, since the flow rate during the separation unit is decreased. By this process, a constant gas flow into the detector can be provided.

The switch of gas flow into the bypass gas line can be preprogrammed, based on the configuration of the system, such as its capacity or volume, and the carrier gas flow rate. As an example, in one configuration, $N_2$ and $CO_2$ gases can be allowed to leave a gas chromatograph column at a first (high) flow rate. After their detection by the detector, gas flow is reduced, by the aforementioned means, so as to allow analytes with a higher retention time, such as $SO_2$ to be concentrated on the column.

It should be appreciated that any desirable portion of gas flow can be split away into the bypass gas line, to suit the purpose of the analysis. Thus, in general, in the range of 1 to 99% of the gas flow can be redirected into the bypass gas line, such as in the range 5 to 90%, 10 to 80%, 10 to 70%, 10 to 60%, 10 to 50%, 20 to 60%, or 30 to 60%. Preferably at least 50%, or at least 60%, or at least 70%, or at least 80%, or at least 90% of the gas flow can be redirected into the bypass gas line.

When multiple separation units are provided, e.g. two or more separation columns, the bypass gas line can be arranged downstream from the first separation column, and upstream from the second separation column, or downstream of two or more separation units.

The system according to the invention can be configured to include at least one controller for controlling valve position of at least one valve. The controller can preferably be adapted so that it can receive an input about at least one system parameter, for example a parameter that reflects the presence and/or absence, concentration, or pressure of gas in the system (e.g., analyte gas and/or carrier gas), and provide a signal to at least one valve based on the parameter information. In some embodiments, the controller is adapted to receive an input about the concentration about at least one analyte gas, and wherein the controller is able to adjust the position of at least one of the valves in the system based on the at least one measuring cell parameter. In some configurations, the controller is adapted to adjust the position of at least one valve, such as at least one switch valve. The valves can therefore also be adapted to be able to receive input from a controller, to change their position depending on the signal from the controller. The controller can also be adapted to receive an input about time that has passed during one or more stages of the system, for example flushing of an autosampler, time since sample was introduced into the receptacle, or delivered by the receptacle, such as an elemental analyzer. The controller can thus be adapted to regulate the position of one or more valves based on sample or analyte gas concentration, sample or analyte gas presence or sample or analyte gas absence, or time parameters. For example, the controller can receive information about the time of purging of the autosampler, and control position of at least one switch valve to prevent recycling and/or venting recycled gas to atmosphere during sample loading. The controller can also be adapted to regulate the position of at least one flow controller, such as a mass flow controller.

The controller can also receive an input about the concentration and/or the presence or absence of at least one analyte gas in the gas outlet line, for example at the detector. Determination of the quantity of at least one gas is used to make a decision about the position of at least one valve in the system. For example, for preconcentrating an analyte gas, the controller can receive information from the detector about the presence of at least one analyte gas, such as $N_2$ and/or $CO_2$, that typically elute first in a separation device such as a gas chromatograph column. The controller subsequently can send a signal to at least one switch valve, that results in a decreased flow into the separation column, due to a part of the gas in the gas outlet line being diverted into the gas recycling line. The controller can simultaneously provide a signal to at least one other switch valve for regulating flow in a bypass line that leads from a gas splitter downstream from the detector, so as to provide a constant gas flow into the detector, while reducing gas flow into the separation column. detection.

The controller can in another embodiment be configured to control the valve position of at least one valve on the recycling line. For example the controller can be configured to open a switch valve on the recycling line to vent gas in the recycling line to air, so as prevent contamination of samples that are to be analysed in the elemental analyser reactor. The controller can preferably use a system parameter such as time for determining of the switch valve.

In certain embodiments, analyte gas in the system according to the invention is provided by an elemental analyser. The analyser can be provided with a carrier gas supply that is used for transporting the analytes that are generated in the chemical reactor of the elemental analyser into the gas outlet line. Moreover, the system can include more than one supply of the carrier gas.

In certain embodiments of the invention, one or more of the junctions of the system are provided as a T-junction. In this context, a T-junction means any junction of three flow channels, i.e. a junction that contains three arms. The T-junction can be provided as a T-piece, as a Y-piece, or as a junction of three orthogonal channels. The junction can further be provided as a two-dimensional junction, wherein the three channels lie within the same plane, or the junction can be provided as a three dimensional structure, in which the three channels do not all lie in the same plane (i.e., as a three-dimensional "tripod").

Components of the system according to the invention, for example the gas inlet line, the gas outlet line, the recycling line, the bypass line, and split lines, and including gas line junctions that are described herein, can be provided in a machined block, i.e. as one mechanical piece. This means that manufacturing of the system can be performed by machining out of a bulk of material, such as a metal block. Further, using T-junctions, with or without manufacturing in a machined block, ensures that flow through the openings in the junction are under full mechanical control. The T-junction design ensures that diffusion paths are well separated, which facilitates setup and calibration of the system, because its flow properties are well determined and predictable.

Further, it should be appreciated that the invention can be combined with gas inlet systems that are known in the art, including for example carrier gas inlet systems, that provide gas flow for transporting gas in analytical systems.

The system according to the invention can be provided in combination with, or include, any suitable on or more detector for detecting gaseous analytes, including any of those described above, or one or more detection unit comprising a separation device and detector, as described above.

It should be appreciated that features described herein in the context of the gas transport system according to the invention are also contemplated in the method according the invention. Accordingly, the method of the invention can be performed using the system according to the invention.

The above features along with additional details of the invention, are described further in the exemplary embodiments below.

BRIEF DESCRIPTION OF THE DRAWINGS

The skilled person will understand that the drawings, described below, are for illustration purposes only. The drawings are not intended to limit the scope of the present teachings in any way.

FIGS. 3A-B show a comparative example of gas savings by the gas transport system of the invention.

DESCRIPTION OF VARIOUS EMBODIMENTS

In the following, exemplary embodiments of the invention will be described, referring to the figures. These examples are provided to provide further understanding of the invention, without limiting its scope.

In the following description, series of steps are described. The skilled person will appreciate that unless required by the context, the order of steps is not critical for the resulting configuration and its effect. Further, it will be apparent to the skilled person that irrespective of the order of steps, the presence or absence of time delay between steps, can be present between some or all of the described steps.

It should be appreciated that the invention is applicable for managing gas consumption in analytical systems requiring a high volume of carrier gas and/or a constant gas flow. Accordingly the invention can be useful in various analytical systems. Further, the system and method according to the invention is illustrated in the embodiments that follow with a preferred embodiment of an elemental analyzer, but it should be appreciated that the invention is also applicable to other analytical systems for gas analysis that would benefit from management of gas consumption. Accordingly, therefore, the gas that is being analyzed and/or the carrier gas in the system will be variable.

Figure 1:
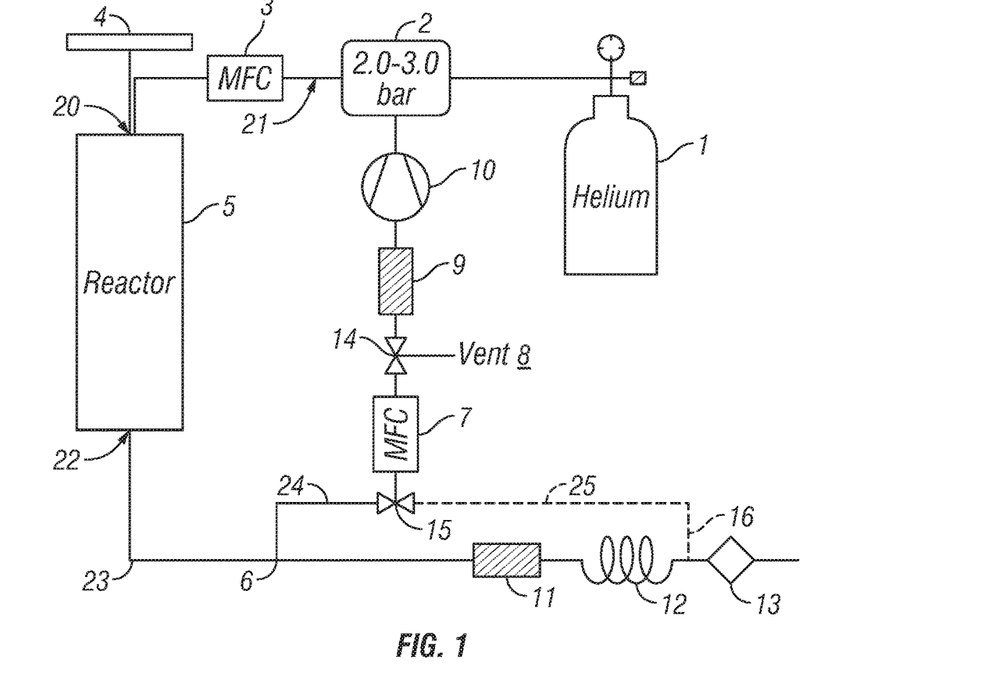
FIG. 1 shows a schematic layout of an elemental analyzer that is interfaced with a gas transport system according to the invention.

Turning to FIG. 1, there is shown an elemental analysis system that includes a reactor 5, e.g. a combustion reactor, for converting samples to be analyzed into sample gases (analyte gases) such as $N_2$, $CO_2$ and $SO_2$. The reactor has an inlet 20 and an outlet 22. Carrier gas, in this example helium gas, flows into the reactor through a carrier gas line 21, and sample gas flows from the reactor through a gas outlet line 23. Gas flow into the reactor is maintained by a mass flow controller (MFC) 3 that is supplied by gas from a volume 2 filled with helium gas at constant pressure, usually about 200-300 kPa. A helium gas supply 1 supplies gas into the volume 2. Samples are introduced into the reactor by an autosampler 4 (or another sample delivery device) in a stream of helium gas. Following sample introduction, the sample is converted to analyte gas that exit through the gas outlet 22 into the gas outlet line 23 in a stream of helium gas. During analysis, gas flow in the system is typically set to about 100 mL/min.

On the gas outlet line there is a first gas line junction 6, that directs a majority (typically in the range 75-95 vol % or 75-90 vol %) of gas flow towards a recycling gas line 24, while a small proportion of the sample gas is directed towards the separation column 12 and the thermal conductivity detector 13. A switch valve 15 is positioned on the recycling gas line, for controlling gas flow through the recycling line. If the switch valve is open to gas flow through the recycling line, a majority of gas flow at the gas line junction 6 will flow into the recycling line. If the recycling line is closed by an alternate position of the switch valve that prevents flow through the recycling line, all gas from the reactor will flow towards the separation column 12. A chemical trap 11 is provided upstream from the separation column, for preventing any $H_2O$ from entering the column. During sample loading, switch valve 15 is open to gas flow through the recycling line. However, during this process, gas in the recycling gas line is vented to atmosphere through an open vent 8 on the recycling line, that is regulated by a switch valve 14. This purge to atmosphere is desired so that sample or analyte gas does not re-enter the reactor via the recycling line 24, where it would contaminate gases produced during combustion of following samples. The switch valve 14 can be controlled by a controller (not shown), that is preferably time-controlled or controlled in response to a signal generated from the analytical portion of the system (e.g. detector). The controller can be configured to receive information about system parameters, such as the concentration and/or the presence or absence of analyte gases at the detector 13.

Following analyte gas generation, i.e. after all sample and analyte gas has passed gas line junction 6, which typically takes about 3 minutes, carrier gas passing through the reactor can be recycled into volume 2. This is done by changing the position of switch valve 14, which now allows gas flow through the recycling line and closes the vent 8.

Gas into the volume 2 from the recycling line is delivered by a compressor 10, which is controlled so as to provide a pressure of 200-300 kPa in the volume 2. Optionally, there can be a trap 9 arranged upstream from the compressor, between the compressor 10 and the switch valve 14, for removing any trace contaminating gases, such as but not limited to $H_2O$, SO2 and/or $CO_2$. There can also optionally be a mass flow controller 7 arranged on the recycling line, for providing further stability to the flow of gas in the recycling line, and that is preferably arranged upstream from the switch valve 14, and downstream from the split valve 15. The recycled carrier gas that flows into the volume 2 is supplemented by gas flow from the helium gas supply 1. Flow of gas in the system can be set to e.g. 100 mL/min. By allowing for example 90% of the gas from the reactor outlet to enter the recycling line, a supplemental gas flow of 10 mL/min from the gas supply 1 will be needed to maintain gas pressure in the volume 2. During recycling, there will therefore be a gas flow of 100 mL/min from the volume 2, 90% of which is gas that has been recycled through the gas recycling line 24. During the entire analysis process there will therefore be a constant gas flow rate of 10 mL/min through the chemical trap 11, the separation column 12 and to the detector 13, which is important for maintaining stable analytical conditions.

In another configuration of the system, the gas recycling line 24 is constructed such that 96.7% of gas flow in the gas outlet line 23 is diverted into the gas recycling line. This means that when the reactor 5 is flushed with for example 300 mL/min of carrier gas, 290 mL/min of the gas is recycled through the gas recycling line 24 into the volume 2 and from there back towards the reactor 5, while gas flow in the downstream analytical portion of the system is maintained at 10 mL/min, which corresponds to 3.3% of the gas flow that emerges from the reactor 5.

One advantage of the system is that it saves large amounts of gas during idle periods, i.e. when the system is not being used for analysis. Thus, reducing gas flow rate to a minimum flow rate of for example 10 mL/min, the switch valve 15 can be set to prevent gas flow into the recycling line, such that the entire volume of gas at the first gas line junction enters the analytical section of the instrument, i.e. separation column, chemical trap, detector and any open slits that can be arranged on the gas outlet line. This means that the system can also be maintained at a very low gas flow rate.

In another configuration of the system, an optional bypass line 25 (dotted lines) is arranged between the separation column 12 and the detector 13. The bypass line is connected to the gas outlet line at a gas flow splitter 16, and to the recycling line at the split valve 15. Accordingly, in this embodiment, the split valve 15 has one position, in which gas flows through the gas recycling line but not the bypass line, and a second position, in which gas flows through the bypass line but not into the recycling line from the first gas line junction 6.

The split valve 15 can be controlled by a controller (not shown), that is preferably time-controlled or controlled in response to a signal generated from the analytical portion of the system (e.g. detector). The controller can be configured to receive information about system parameters, such as the concentration and/or the presence or absence of analyte gases at the detector 13.

The bypass line is useful for allowing preconcentration of analyte gas samples that emerge from the reactor 5. Thus, during sample loading, analyte gas is provided through the gas outlet line 23 at a flow rate of 10 mL/min for example. Gas flow into the recycling line 24 through the first gas line junction 6 is prevented by switch valve 15. Therefore, the entire gas stream passes through the separation column 12, and the optional chemical trap 11. The switch valve 15 however is open to gas flow from the gas flow splitter 16, through the bypass line 25, from which the gas reaches the recycling line and is vented to air through the open vent 8. Allowing half of the gas flow to enter the bypass line 25 results in a flowrate at the detector 13 of 5 mL/min. To concentrate desired analyte gases, the splitter 16 remains open until the desired analyte gas has passed the first gas line junction 6 and before it exits the separation column 12. By changing position of the switch valve 15, gas flow through the first gas line junction 6 is allowed into the recycling line 24, and simultaneously gas flow into the bypass gas line 25 is prevented. The recycling line is configured such that also half of the incoming gas flow is directed into the recycling line. This results in a decreased gas flow through the separation column 12 of 5 mL/min, which results in an effective two-fold increase in concentration of the analyte as it exits the separation column. Throughout this process, the gas flow rate at the detector 13 remains constant at 5 mL/min.

Since sulfur is usually a much less abundant element than carbon and nitrogen in analyte samples (e.g. in typical organic, environmental, biological samples), which means that much less $SO_2$ is generated compared with $N_2$ and $CO_2$, it can be advantageous to concentrate $SO_2$ before analysis. Since $N_2$ and $CO_2$ migrate faster than $SO_2$ through typical gas chromatogram columns, it can be advantageous to allow $N_2$ to $CO_2$ to pass through the column and the detector, while splitting away a part of the gas through the splitter 16 and the bypass line 25. After $N_2$ and $CO_2$ have passed the splitter 16, gas flow can be changed by adjusting the position of the split valve 15, so as to concentrate $SO_2$ on the column. This way, an increased sensitivity for $SO_2$ is achieved.

Figure 2:
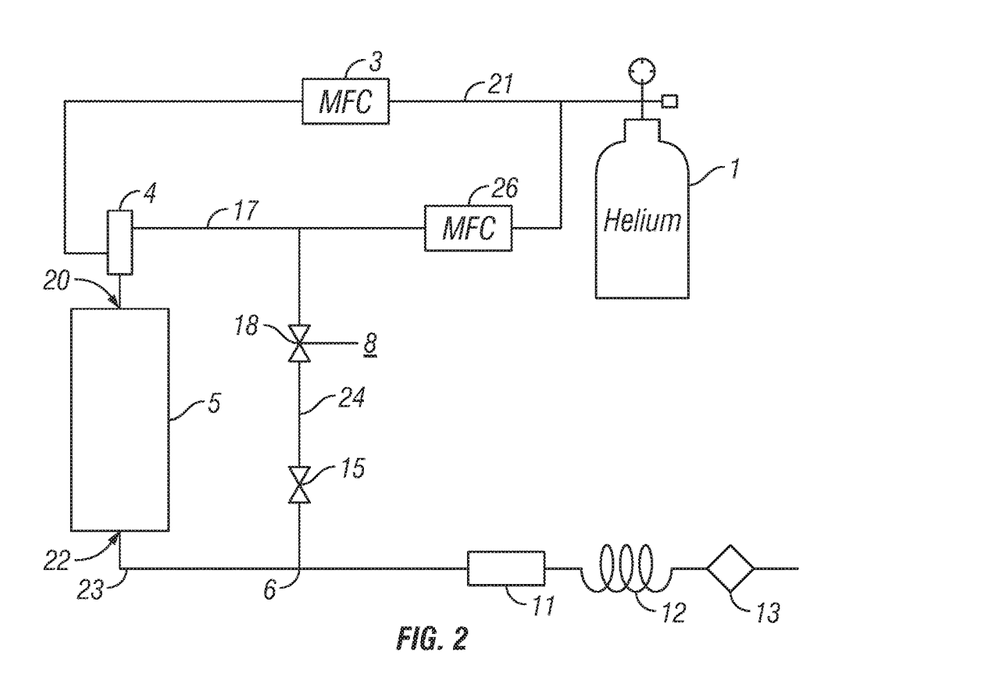
FIG. 2 shows an alternative layout that includes a recycling line that feeds into a gas purge line for the autosampler.

Another variation of the system according to the invention is illustrated by the schematic drawing of FIG. 2. A gas purge line 17 is split away from the carrier gas inlet line 21, to provide a gas purge into the autosampler 4. Gas flow in the gas purge line is regulated by a mass flow controller 26. A switch valve 15, for controlling gas flow into the gas recycling line, is arranged on the gas recycling line. The recycling line feeds into the gas purge line 17, so that recycled gas within the system is used for purging the autosampler 4. In a typical operation, a large purge of the autosampler is required prior to injection. Thus, there can typically be a carrier gas flow of 180 mL/min into the reactor, controlled by the mass flow controller 3, and a total amount of gas flow needed for purge of for example 200 mL/min. At the first gas line junction 6, a large portion (90%) of the gas in the gas outlet line 23 is diverted into the gas recycling line through the open switch valve 15. During this mode, approx. 162 mL/min of the gas from the reactor 5 is recycled and used for purging the autosampler 4. The additional approx. 38 mL/min that are needed for purging are provided by the carrier gas supply, and regulated by the mass flow controller 26. During this time, the gas flow in the analytical portion, the chemical trap 11, separation column 12 and detector 13, is 18 mL/min, or 10% of the carrier gas flow into the reactor 5. Following the injection of sample into the reactor, typically until substantially all sample or analyte has passed gas line junction 6, the switch valve 15 is closed. At the same time, the flow rate into the reactor is reduced to 18 mL/min (by adjustment of MFC 3), so that the gas flow through the analytical portion of the system remains constant.

Optionally, there can be a switch valve 18, for controlling gas flow through the open vent 8. By opening the switch valve 18, gas will flow through the open vent, and thus be vented to atmosphere. This can be useful, e.g. during sample loading to prevent overloading of the separation column 12, and thus prevent or minimize sample overload effects. Furthermore, by splitting a portion of the sample gas to flow through the recycling line to the open vent 8, there will be reduced load on the chemical trap 11, thus extending the lifetime of the chemical trap. The switch valve 18 can be controlled by a controller (not shown), that is preferably time-controlled. The controller can also be configured to receive information about system parameters, such as the concentration and/or the presence or absence of analyte gases at the detector 13. There may be also be in this embodiment, similar as in the embodiment of FIG. 1, arranged a trap (not shown) in the recycling line, anywhere between junctions 6 and 17, for adsorbing polar gases like CO2, SO2 and/o H2O (e.g. an Ascarite trap). This has the same advantages as in the embodiment of FIG. 1, of further reducing the memory effects of those gases.

Figure 3A:
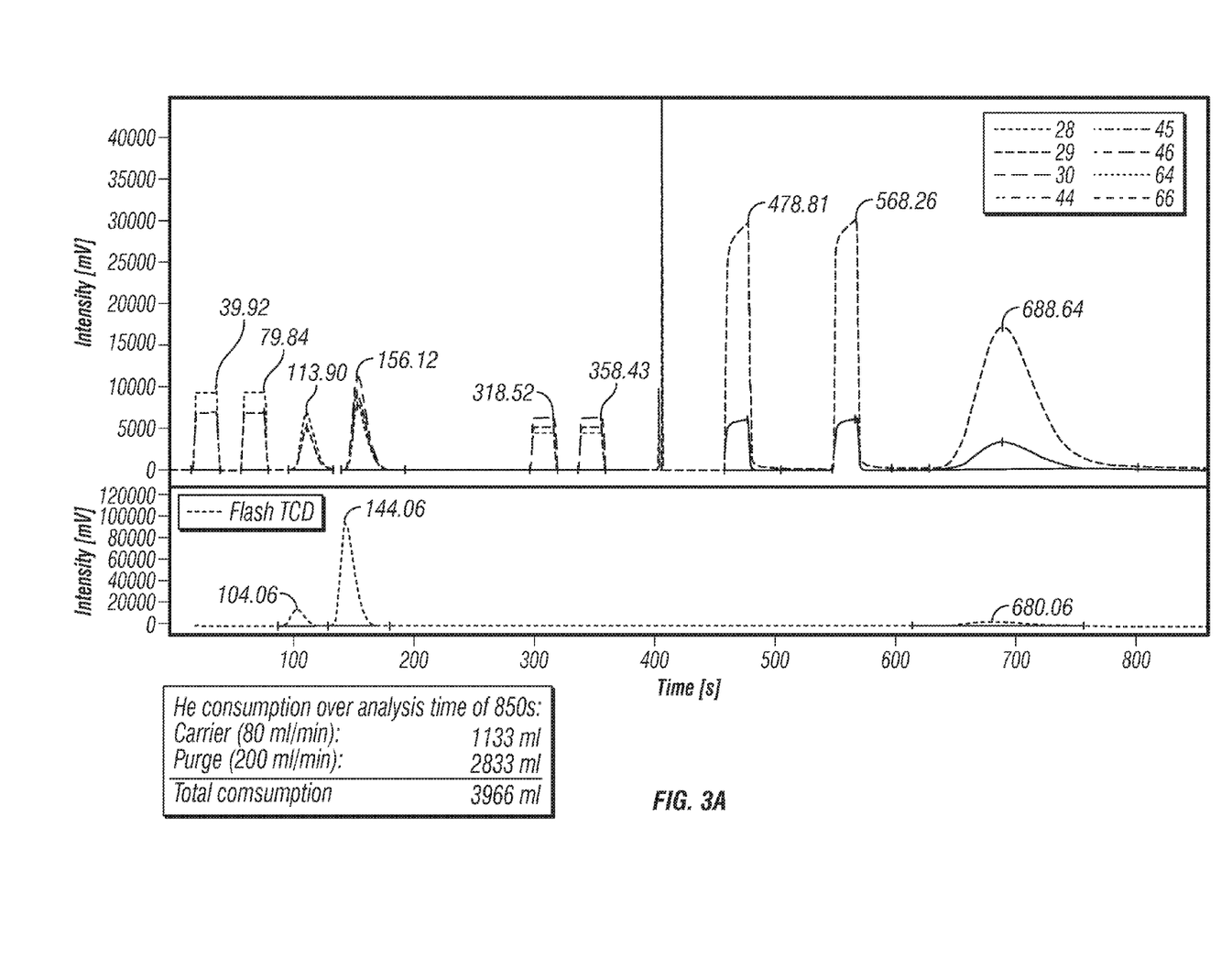
FIG. 3A shows conventional flushing over an analysis period of 850 seconds.
Figure 3B:
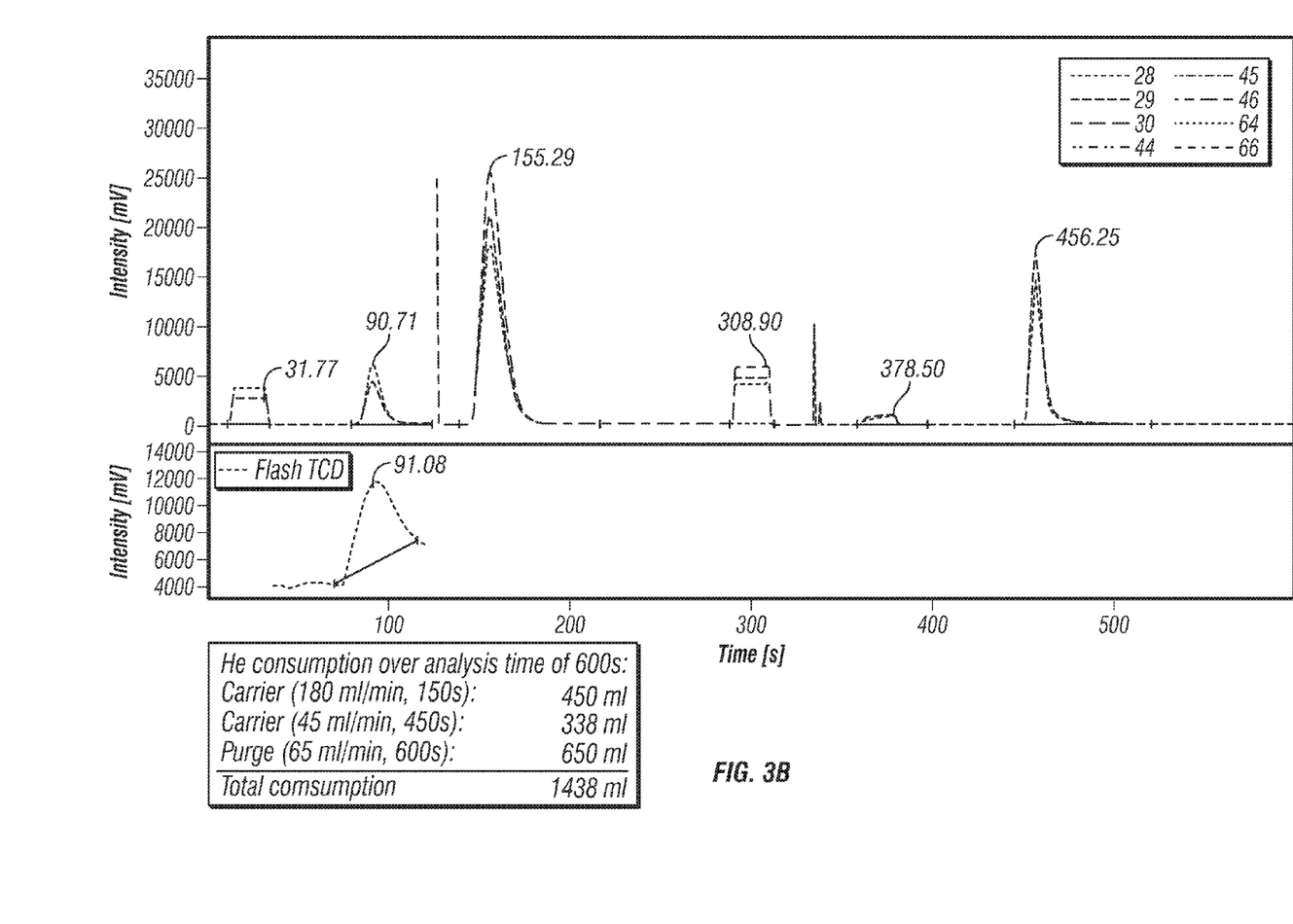
FIG. 3B shows flushing using a recycling line over a total analysis period of 600 seconds.

As can be appreciated, an advantage of the system is that by recycling a large portion of the gas flow during the purging mode, a large amount of carrier gas is saved, compared with systems that do not recycle gas. An example of the gas savings provided by the system according to the invention is provided by FIG. 3. The data is produced for a conventional elemental analyzer (comprising a heated reactor) that is connected to an autosampler, a gas chromatography column and a thermal conductivity detector. A recycling line is provided, that can recycle gas from the gas outlet line of the analyzer to the purge line.

In (A), helium consumption during a conventional performance of an elemental analyzer is shown, i.e. there is no recycling. Results are shown for an analysis of 559 μg of sulfanilamide, that results in formation of $N_2$, $CO_2$ and $SO_2$ gas. A constant flow of carrier gas of 80 mL/min is provided in the system, for a total consumption of 1133 mL over 850 seconds analysis time. Furthermore, the autosampler is purged by a constant flow of 200 mL/min, for a total consumption of 2833 mL. In total therefore, the gas consumption over the analysis period is 3966 mL.

Turning to (B), analysis of 422 μg of sulfanilamide is shown. There is an initial helium gas flow of 180 mL/min into the reactor, 135 mL/min of which (75%) is recycled into the purge line for purging the autosampler, and 45 mL/min is used for constantly flushing the separation column and detector. A total purge flow rate of 200 mL/min into the autosampler is achieved by supplementing the flow of 135 mL/min from the recycling line by 65 mL/min of helium from the helium tank. After 150 seconds, carrier gas flow is reduced to 45 mL/min, and the split valve is closed to prevent recycling of sample gases into the autosampler. The autosampler is at this point flushed by the 65 mL/min gas stream from the helium tank, while the rest of the system is continuously flushed with 45 mL/min helium flow. The total gas consumption during the analysis period of 600 seconds is 1438 mL, or about 36% of the gas consumption during conventional operation. A further advantage in this example is the reduced analysis time of 600 seconds, which is achieved by improving separation on the gas chromatography column, by ramping the temperature up for fast elution of $SO_2$ from the column.

As should be appreciated based on the foregoing description of the invention and some of its embodiments, the invention provides distinct advantages over gas systems that are known in the art. Some of these advantages include:

reduction of carrier gas consumption, for example helium, in analytical systems such as elemental analyzers, based on the splitting of gas flow to allow recycling of a large proportion of the helium gas in the system.

Reduced cost of operating analytical systems, due to less carrier gas consumption. The consumption of helium in elemental analyzers can be reduced by more than 50% by the system according the invention.

A simplified gas flow system, compared with alternative carrier gas systems that include hardware modifications, including use of different detectors and mass flow controllers, that come along with using alternative carrier gas types such as argon.

Reduced flow conditions in the system during standby mode without risk of undersupply of any sections of the system.

Extended life time of chemical traps downstream from the recycling split, because of the significantly reduced gas load in the chemical trap.

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components.

It will be appreciated that variations to the foregoing embodiments of the invention can be made while still falling with the scope of the invention can be made while still falling within scope of the invention. Features disclosed in the specification, unless stated otherwise, can be replaced by alternative features serving the same, equivalent or similar purpose. Thus, unless stated otherwise, each feature disclosed represents one example of a generic series of equivalent or similar features.

Use of exemplary language, such as "for instance", "such as", "for example" and the like, is merely intended to better illustrate the invention and does not indicate a limitation on the scope of the invention unless so claimed. Any steps described in the specification may be performed in any order or simultaneously, unless the context clearly indicates otherwise.

All of the features and/or steps disclosed in the specification can be combined in any combination, except for combinations where at least some of the features and/or steps are mutually exclusive. In particular, preferred features of the invention are applicable to all aspects of the invention and may be used in any combination.

The invention claimed is:

1. A gas transport system for continuously flushing a chemical reactor, comprising:
    the chemical reactor, the chemical reactor having an inlet and a gas outlet, the inlet for introducing a sample and a carrier gas into the chemical reactor, and the gas outlet for releasing an analyte gas and the carrier gas from the chemical reactor;
    a sample introduction unit for delivering the sample into the chemical reactor;
    a carrier gas line fluidly coupled to the inlet, the carrier gas line for introducing the carrier gas from a carrier gas source into the chemical reactor;
    a gas outlet line from the gas outlet;
    a gas recycling line connected to the gas outlet and/or the gas outlet line by a first gas line junction that is arranged between the chemical reactor and a downstream detection unit coupled to the gas outlet line, and connected to the sample introduction unit and/or the inlet and/or the carrier gas line at a second gas line junction;
    the detection unit, wherein the detection unit includes a separation unit and a detector downstream of said separation unit, the separation unit is connected to the gas outlet line downstream of the first gas line junction, and the separation unit includes a chromatographic column; and
    a gas flow splitter downstream of the separation unit, the gas flow splitter configured for splitting a gas flow stream exiting the separation unit into a first gas stream entering a bypass gas line and a second gas stream entering the detector, the bypass gas line being fluidly connected to the gas recycling line,
    wherein the gas transport system is adapted to allow recycling of at least a portion of gas emerging from the gas outlet back to the chemical reactor via the gas recycling line.

2. The gas transport system of claim 1, wherein the gas recycling line is connected to the gas outlet line or the gas outlet at the first gas line junction, between the chemical reactor and the detection unit, and to the carrier gas line at a second gas line junction.

3. The gas transport system of claim 1, wherein the carrier gas line comprises at least one in-line gas reservoir to which the gas recycling line is connected.

4. The gas transport system of claim 1, wherein the inlet comprises a carrier gas inlet and a sample inlet.

5. The gas transport system of claim 1, wherein the chemical reactor is selected from a combustion reactor, a reduction reactor and a pyrolysis chamber.

6. The gas transport system of claim 1, wherein the sample introduction unit comprises a sample introduction device and a gas purge line, the gas purge line adapted to provide a stream of gas into the sample introduction device.

7. The gas transport system of claim 6, wherein the gas recycling line is connected to the gas purge line, enabling recycling of at least a portion of gas exiting the reactor as purging gas for purging the sample introduction device.

8. The gas transport system of claim 6, comprising one or more flow control units for controlling flow of gas fed into the gas purge line.

9. The gas transport system of claim 8 wherein said one or more flow control units comprise first mass flow controller for controlling flow of carrier gas in the carrier gas line, and a second mass flow controller for controlling flow in the gas purge line.

10. The gas transport system of claim 1, comprising a valve arranged on the gas recycling line or at the first gas line junction, for controlling gas flow in the gas recycling line.

11. The gas transport system of claim 1, further comprising at least one chemical trap arranged on the gas recycling line.

12. The gas transport system according to claim 11, wherein the gas recycling line comprises a recycling split valve upstream of the chemical trap, the recycling split valve having a first position allowing gas to flow through the gas recycling line, and a second position in which gas is prevented from flowing through the gas recycling line.

13. The gas transport system according to claim 12, further comprising an open vent that is fluidly connected to the recycling split valve, and wherein the recycling split valve releases gas through the open vent in the second position.

14. The gas transport system of claim 1, comprising a flow controller arranged on the gas recycling line.

15. The gas transport system of claim 1, wherein the gas recycling line is configured so that during recycling, in the range of about 1-50 vol % of gas from the gas outlet is directed onwards through the gas outlet line and in the range of 50-99 vol % of gas from the gas outlet is directed to the gas recycling line.

16. The gas transport system of claim 1, wherein the gas recycling line is configured so that when total gas flow from the gas outlet is in the range of about 80 to about 1000 mL/min, in the range of about 5-35 mL/min of gas passes through said first gas line junction onwards through the gas outlet line during recycling.

17. The gas transport system of claim 1, comprising a compressor arranged on the gas recycling line, to increase the pressure of gas passed through the gas recycling line to the carrier gas line and/or the sample introduction unit.

18. The gas transport system of claim 1, wherein the detector is selected from the group consisting of a mass spectrometer, a thermal conductivity detector, and an optical spectrometer.

19. The gas transport system of claim 1, comprising a valve for controlling gas flow in the bypass gas line, wherein said valve is a switch valve, connecting the bypass gas line to the gas recycling line, the switch valve having at least two positions wherein a first position allows flow from the first gas flow junction through the gas recycling line and prevents flow of gas from the bypass gas line to the gas recycling line, and a second position preventing flow from the first gas line junction to the gas recycling line and allowing flow from the bypass gas line to the gas recycling line.

20. The gas transport system of claim 1, further comprising a controller for controlling a valve position of at least one valve, wherein the controller is adapted to receive an input of at least one system parameter selected from gas concentration in the detector, presence and/or absence of a gas in the detector, and time, and wherein the controller is able to adjust the valve position of the at least one valve based on the at least one system parameter.

21. The gas transport system of claim 20, wherein the controller is configured to control the valve position of the at least one valve so that in a first position gas is directed to flow through the gas recycling line towards the carrier gas line and/or the sample introduction unit and so that in a second position gas is prevented from flowing through the gas recycling line.

22. A method for managing gas consumption in a continuously flushed elemental analyzer, the method comprising steps of:
(i) streaming carrier gas through a carrier gas line into a chemical reactor;
(ii) introducing a sample from a sample introduction unit into the chemical reactor;
(iii) directing a gas flow from a gas outlet on the chemical reactor through a gas outlet line;
(iv) splitting the gas flow at a first gas flow junction in the gas outlet or gas outlet line, between the chemical reactor and a downstream detection unit, to direct a portion of the gas flow to a gas recycling line leading to the carrier gas line and/or the sample introduction unit and/or the chemical reactor, and a remaining portion of the gas flow onwards through the gas outlet line towards the detection unit, wherein the detection unit comprises a separation unit and a detector downstream of the separation unit; and
(v) splitting away a part of a gas stream from the separation unit through a gas bypass line that is connected to the gas outlet line downstream from the separation unit and is connected to the gas recycling line, such that the gas stream exiting the separation unit is split into a gas stream entering the gas bypass line and a gas stream entering the detector.

23. The method of claim 22, comprising directing at least a portion of the gas flow from the gas outlet to the gas recycling line and through the gas recycling line to a gas purging line, which is part of the sample introduction unit, to purge the sample introduction unit.

24. The method of claim 22, further comprising for a first period of time following the introduction of sample into the chemical reactor, a step of reducing or preventing flow of gas in the gas recycling line to the carrier gas line and/or the sample introduction unit and/or the chemical reactor.

25. The method of claim 22, further comprising directing gas flow from the gas bypass line to the gas recycling line.

26. The method of claim 25, further comprising a step of preventing flow through said gas recycling line from the first gas line junction and directing all gas exiting the gas outlet through the gas outlet line towards the detection unit, passing the gas flow through the separation unit arranged on the gas outlet line, and allowing at least a portion of gas flowing through the separation unit to flow through the gas bypass line.

27. The method of claim 22, further comprising venting from the gas bypass line, not recycling, the portion of the gas flowing through the separation unit until substantially all sample has disappeared from the portion of the gas flowing through the separation device.

28. The method of claim 27, wherein after a period of flowing a portion of gas through the gas bypass line, flow of gas through the gas bypass line is prevented and flow of gas through said gas recycling line from the first gas line junction is allowed.

* * * * *

UNITED STATES PATENT AND TRADEMARK OFFICE
CERTIFICATE OF CORRECTION

PATENT NO. : 10,338,044 B2
APPLICATION NO. : 15/142909
DATED : July 2, 2019
INVENTOR(S) : Johannes Schwieters

Page 1 of 1

It is certified that error appears in the above-identified patent and that said Letters Patent is hereby corrected as shown below:

In the Claims

Claim 9, Column 18, Line 45:
Replace "flow control units comprise first mass flow"
With --flow control units comprise a first mass flow--

Signed and Sealed this
Nineteenth Day of November, 2019

Andrei Iancu
*Director of the United States Patent and Trademark Office*